United States Patent [19]

Kraft et al.

[11] Patent Number: 4,819,657
[45] Date of Patent: Apr. 11, 1989

[54] AUTOMATIC ALLERGY DETECTION SYSTEM

[75] Inventors: Thomas L. Kraft, Houston; Howard A. Vick, Missouri City; James W. Meador, Houston, all of Tex.

[73] Assignee: KVM Engineering, Inc., Houston, Tex.

[21] Appl. No.: 60,974

[22] Filed: Jun. 16, 1987

Related U.S. Application Data

[63] Continuation of Ser. No. 722,798, Apr. 12, 1985, abandoned.

[51] Int. Cl.$^4$ ............................................. A61M 37/00
[52] U.S. Cl. ..................................... 128/736; 128/743; 604/20
[58] Field of Search ............ 128/736, 743, 664, 414 R

[56] References Cited

U.S. PATENT DOCUMENTS

| | | | |
|---|---|---|---|
| 2,304,817 | 12/1942 | Grozin | 128/743 |
| 3,623,473 | 11/1971 | Andersen et al. | 128/736 |
| 4,055,166 | 10/1977 | Simpson et al. | 128/736 |
| 4,253,334 | 3/1981 | Hakansson et al. | 128/736 |
| 4,270,547 | 6/1981 | Steffen et al. | 128/736 |
| 4,390,022 | 6/1986 | Calfee et al. | 128/429 PG |
| 4,396,020 | 8/1983 | Wolff et al. | 128/736 |
| 4,445,516 | 5/1984 | Wollnik et al. | 128/736 |
| 4,461,301 | 7/1984 | Ochs | 128/736 |
| 4,488,560 | 12/1984 | Takamura | 128/736 |
| 4,503,862 | 3/1985 | Baessler | 128/736 |

OTHER PUBLICATIONS

"Stedman's Medical Dictionary", 24th ed, Waverly Press, Baltimore, Md., 1982.
"The Use of Differential Skin-Temperature Measurements in the Evaluation of Post-Traumatic Oldema Control", by Hambury et al., Med. & Biol. Eng., vol. 13, No. 2, Mar. 1975, pp. 202-208.

Primary Examiner—Lee S. Cohen
Assistant Examiner—David Shay
Attorney, Agent, or Firm—Tim L. Burgess

[57] ABSTRACT

Disclosed herein is an automatic allergy testing system. The system includes an electrode capable of testing up to eight different allergies and an associated electronic unit. The electrode includes apparatus to transcutaneously deliver an allergen to the patient without puncturing the patient's skin. The electrode also includes a temperature sensor for sensing the skin temperature in the area surrounding the delivery of the allergen. Electronic apparatus is provided for processing the sensed temperature and storing data related thereto for subsequent print out to an output device. The allergy testing system is controlled so that periodic temperature readings are made at thrity second intervals over approximately a fifteen minute testing span. The data can be printed out in a graphic format to allow the physician to easily and quickly make more accurate diagnosis.

41 Claims, 3 Drawing Sheets

AUTOMATIC ALLERGY DETECTION SYSTEM

This is a continuation of co-pending application Ser. No. 722,798 filed on Apr. 12, 1985, now abandoned.

This invention relates to an automatic allergy detection system, and more particularly to such a system in which an allergic reaction is automatically tested by measuring the temperature of any wheal surrounding the allergen application and thereafter processing the sensed temperature data for output in a useable format.

Allergy testing in the past has generally been accomplished by the use of some skin test, the most traditional method being a scratch test, in which a small scratch is placed on the skin and an allergen in placed over the scratch. The allergen enters the area of the body beneath the skin and if the person being tested is allergic to the substance of the allergen, a reaction occurs. This reaction is identified by a large wheal or welt occuring in the area surrounding the reaction. The physician diagnoses an allergic reaction by visually inspecting the back and noting the particular wheals formed. It is difficult for the physcan to measure qualitatively the degree of the reaction by the normal observable diagnosis techniques used. The physician may have a general idea of the degree by noting the size of the wheal, but little else is available to assist the physician in accurately diagnosing the degree of reaction occurring.

Other techniques used in the past to diagnose allergy include an injection by a needle puncturing the skin of the allergen. The diagnosing techniques are quite similar to those discussed above with respect to the scratch test. However, the amount of allergen can be more accurately controlled by this technique and the doctor is able to obtain better qualitative analysis results of the degree of reaction. This particularly is true where the doctor injects a plurality of different concentrations or amounts of allergen at different points on the patient. The final prior art technique used to diagnose allergic reactions is the RAST test, which is a blood test run on blood serum.

Many problems exist with the prior art techniques of diagnosing allergic reactions. First, the testing procedure is generally painful to the patient, primarily due to the fact that the skin must be punctured by either the scratch or the needle in order to force the allergen beneath the skin. Second, and more important, a certain risk exists to a patient due to injection or severe allergic reactions. While a typical reaction involves a relatively small wheal which may appear to be the size of an insect bite, severe reactions can cause a patient to go into anaphalactic shock or other similar symptoms.

The RAST test, while not susceptible to some of these difficulties, is very expensive and time consuming so that immediate results are not available to the physician.

In co-pending application U.S. patent application Ser. No. 722,772, filed even data herewith, (File 5804,3804) and assigned to the present assignee hereof, there is described a new and unique electrode which can be used in allergy testing. This electrode allows the allergen to be transcutaneously delivered to the patient without fracturing the skin. It further includes temperature sensing means for sensing the temperature in the area immediately surrounding the point where the allergen was delivered. This electrode is useful in providing additional information to an electronic unit relating to the rise in temperature with respect to time of the reaction area. By displaying this information, the physician can make a better qualitative determination of the degree of the reaction.

The prior art has suggested using the temperature of the reaction area to diagnose the occurrence of an allergic reaction. For example in an article entitled "Use of Thermography in Clinical Allergy" appearing in Vol. 15, No. 5 of the Journal of Allergy Clinical Immunology, Nov. 1972, by Chintana Sphipatanakul, M.D. and Raymond G. Slavin, M.D. both of Saint Louis, MO., a technique of thermographic scanning of a body to detect the pressure of additional heat on the skin surface is described. The detection of heat can be an indication of an allergic reaction where a thermographic scan is of a patient having undergone traditional allergy scratch tests. The problem however is that the qualitative information to make a more complete diagnosis is missing. The thermographic technique can merely scan and detect the reaction; it is not useful in detecting the degree of the reaction.

In accordance with one aspect of this invention, there is provided an allergy testing system for use in conjunction with an electrode which senses the instantaneous skin temperature in the area of an allergic reaction and provides an electric signal manifesting the sensed temperature. The system comprises means for receiving the electric signal, and means for sampling the received signal during a plurality of time and for storing data manifesting the sensed temperature during each sampling. In addition, the system includes means for providing an output indicating a change in temperature with respect to time of the sensed area.

In accordance with another aspect of this invention, there is provided a method of testing a patient for allergic reaction comprising the steps of delivering an allergen beneath the skin of the patient in a test area and measuring the temperature of the skin in the test area during the plurality of times. The method additionally includes the steps of manifesting the temperature change with respect to time relationship of the test area as an indication of an allergic reaction.

One preferred embodiment of the subject invention is hereafter described with specific reference being made to the following Figures, in which.

Figure 1:
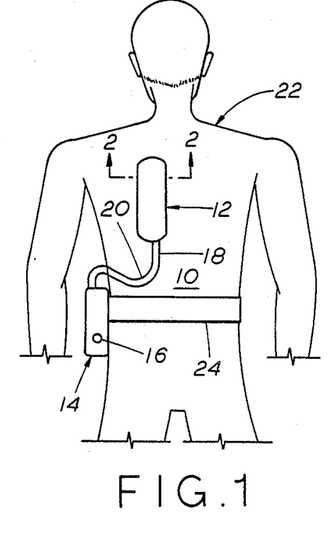
FIG. 1 shows a patient undergoing an allergy test with the electrode and electronic uit of the subject invention.

Referring now to FIG. 1 allergy testing system 10 is shown as including an allergy testing electrode 12 and allergy testing unit 14. Unit 14 includes a start switch 16 and is coupled to electrode 12 by a temperature sensing lead 18 and a charging lead 20. Electrode 12 may be placed at any convenient place on a patient 22, such as the back as shown in FIG. 1 or the arm or other areas in which it is desired to perform an allergy test. Electronic unit 14 may be held around the patient's waist by a belt 24 or may rest in the patient's lap.

As will be explained in more detail hereafter, electrode 12 is prepared and placed on patient 22 at the desired place. Wires 18 and 20 are then connected to electronic unit 14 and switch 16 is depressed. The patient is then sent to the waiting room to wait. Approximately fifteen minutes later the test has been completed and unit 14 is disconnected from electrode 12 and returned to the doctor. Electrode 12 is then removed from the patient and the test is concluded. Thereafter, an output means may be coupled to unit 14 to allow the physician to review the results of the test.

For slow acting allergies, the patient may return home with the unit attached as described. After a period prescribed by the physician, the unit 14 can be removed and returned to the physician for analysis and diagnosis.

Figure 2:
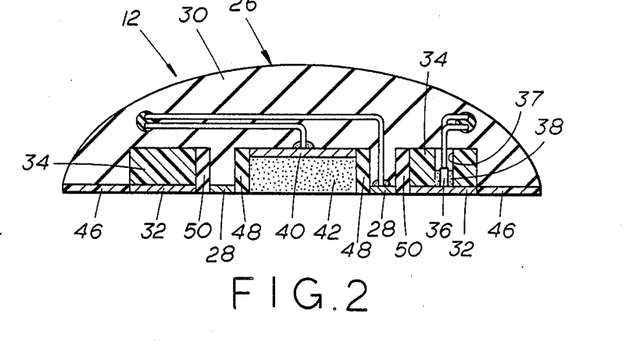
FIG. 2 shows a more detailed diagram of the electrode of the subject invention.

Referring now to FIG. 2, the detailed construction of one of the allergy testing electrodes 26 is shown, it being understood that each of the other electrodes 26 is substantially identical in construction. Each of the electrodes 26 is contained in a common housing 30, which is a part of electrode 12. Housing 30 may be a generally soft material and is both an electrical and thermal insulator. On the bottom of electrode 26, a thin film temperature sensor material 32 is positioned on a thermally insulating base 34. Both material 32 and base 34 may be annular rings having a center opening therein. Material 32 is selected to be a type which can withstand a cleaning solution generally associated with testing. It further should be a type which can have materials soldered or bonded thereto. It has been found that platinum alloys, stainless steel and ceramics are useful materials for this purpose. Base 34 may be any of a variety of well known heat insulating plastic materials. Base 34 should be generally rigid so as to adequately support the thin film temperature sensor 32. Sensor 32 may be either vacuum deposited over base 34 or be a thin integral member secured thereto by gluing or other adhesive techniques.

A temperature to voltage transducer, such as thermister 36, is soldered to plate 32 through a hole 37 is base 34. A thermal bonding material 38 is placed within the hole 37 to thermally bonds thermister 36 with plate 32. A pair of leads from wire 18 is coupled to the leads from thermister 36. As is well known in the art, a thermister is a type of resistor which has a decreasing resistance as the temperature of the surrounding area increases. Thus a thermister can be coupled in circuit with other electronic components and a signal can be generated having a voltage proportional to the temperature of the surrounding area. It also is possible to replace thermister 36 with a thermocouple device which operates by providing a voltage based on the difference in temperature between the two ends thereof.

A permanent charge plate 40 and removable allergen pad 42 are placed within the opening of the annular ring of sensor 32 and base 34. Charge plate 40 is coupled to the voltage carrying lead from charging lead 20. A small change of between 1 and 4 milliamps is provided over lead 20 to charging plate 40. Allergen pad 42 may be a porous material into which a dry allergen is impregnated. Prior to use, a drop of distilled water may be placed on allergen pad 42 to hydrolize the allergen. When pad 42 is placed in contact with the skin of patient 22 and plate 40 receives a charge from lead 20, the allergen contained within pad 42 is transcutaneously delivered beneath the skin of patient 22. It should be noted that it is unnecessary to create any break in the skin of the patient 22.

To prevent the current from traversing a long path into a common electrode, which path would traverse muscles thereby causing pain, a common return electrode 28 is also positioned in the opening of the sensor 32 annular ring. Return electrode 28 is electrically separated from charging plate 40 by an insulator 48 and from sensor 32 by an insulator 50. An electric field is established between charge plate 40 and return electrode 28 through the skin of patient 22. The allergen molecules attach to the electrons in the solution and are drawn through the pores of the skin as the electric field traverses through the skin.

The edges of electrode 12 are covered with a double sided tape 46 which can be used to affix electrode 12 to the desired area on patient 22. Tape 46 may be specially fabricated to fit over all non-electrode 26 areas of electrode 12 so that each of the electrodes 26 and the common electrode are firmly attached against the skin of patient 22.

Figure 3:
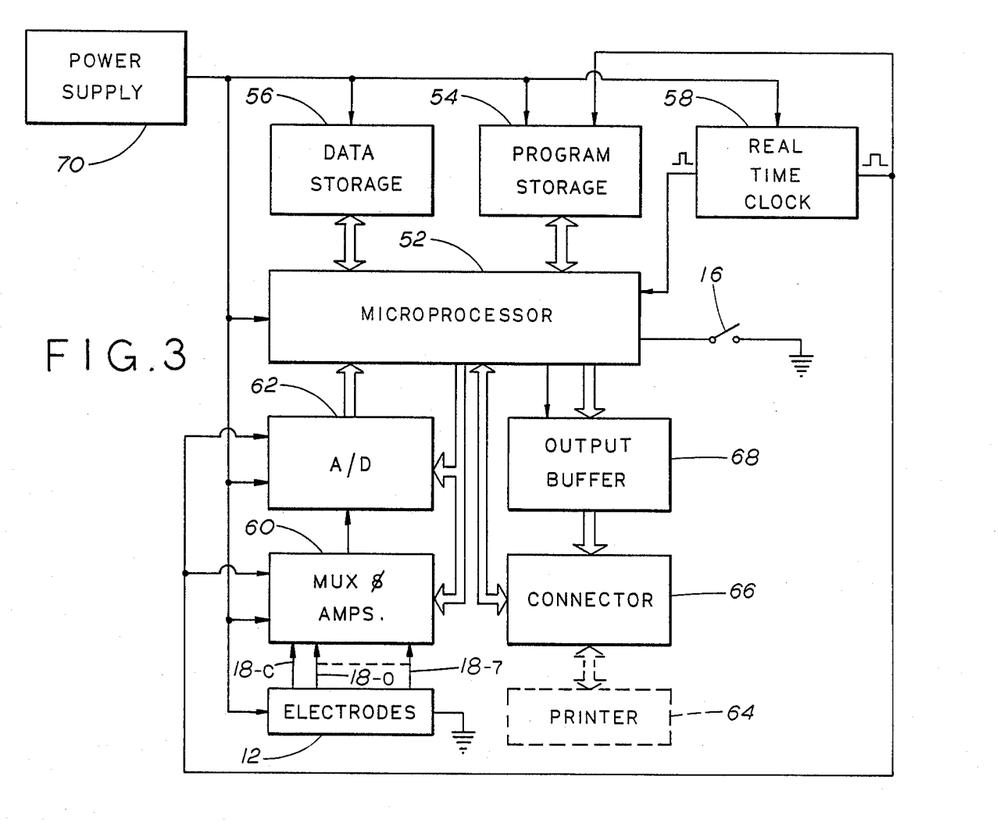
FIG. 3 shows a block diagram of the electronic unit used in the subject invention.

Referring now to FIG. 3, a block diagram of electronic unit 14 is shown. The heart of electronic unit 14 is a microprocessor 52 which controls the reception of information and the transmission of information. The specific operation of microprocessor 52 is under the control of an instruction set contained in program storage memory 54. Program storage memory 54 is connected by data and address buses to microprocessor 52 in a known manner. The data obtained by microprocessor 52 is stored in a data storage memory 56 which may be a conventional random access memory. Again, data storage memory 56 is coupled to microprocessor 52 by data and address buses in a normal manner.

In order to initiate the action of microprocessor 52, switch 16 is depressed, causing an external interrupt reset of microprocessor 52. Thereafter, the time at which microprocessor 52 samples the data provided from electrode unit 12 is internally controlled by real time clock 58. For example, an internal reset pulse may be provided from real time clock 58 every thirty seconds to again reset microprocessor 52 to the beginning of a program cycle causing new data to be sampled and stored in data storage 56. After the appropriate number of samplings have occurred, microprocessor 52 can either disable further responses to the time clock 58 pulses, or it can communicate with real time clock 58 to cause it to cease providing internal reset pulses.

The data path for the temperature data is provided from electrodes 12 over leads 18 to multiplexer and amplifiers 60. As previously mentioned, eight sensed temperature signals 18-0 through 18-7 and one common or normal temperature signal 18-C are provided from electrodes 12 to the amplifiers within multiplexer and amplifiers 60. The amplifiers may be differential amplifiers and the common signal over lead 18-C is provided to one side of each of the differential amplifiers. The voltage signal from a different one of each of the individual testing electrodes 26 on leads 18-0 through 18-7 is provided to the other side of each differential amplifier so that the output of each differential amplifier manifests the rise in skin temperature as a result of any allergic reaction for an associated allergy test. The multiplexer portion of multiplexers and amplifiers 60 is controlled by micrprocessor 52 to provide a selected one of the eight different signals at the output thereof.

The output selected by microprocessor 52 from multiplexer and amplifier 60 is provided to analog to digital converter 62 which converts the analog voltage manifesting the temperature rise into a digital signal, which in turn is provided to microprocessor 52. Microprocessor 52 controls the operation of analog to digital converter 62 by appropriate control signals therefrom. Once the digital data is provided from analog to digital converter 62 to microprocessor 52, microprocessor 52 notes the particular time and date of occurrence when the data was provided and stores both the data and the noted time and date of occurrence in data storage 56. This process continues for each of the eight testing electrodes during each sample times a determined by real time clock 58. These data can be stored for many years with an appropriate patient identification tag. This prevents data or reaction comparisons during certain therapy such as desensitization.

After all of the data has been obtained by microprocessor 52, the physician will desire to inspect visually the information. This can occur by attaching a printer 64 or other output device to a connector 66 associated with electronic unit 14. Connector 66 is attached to microprocessor 52 through an output buffer 68 which receives information and control from microprocessor 52. Additional control lines from microprocessor 52 are also directly connected to connector 66 for the purpose of controlling printer 64. In order to receive the data, switch 16 is again depressed and microprocessor 52 determines that the unit is connected to connector 66. This causes microprocessor 52 to go through an instruction set causing the data stored in data storage 56 to be provided through output buffer 68 to connector 66 and from connector 66 to the output device such as printer 64.

Power is supplied to each of the various modules shown in FIG. 3 from a power supply 70. Because it is desirable that electronic unit 14 be portable, power supply 70 typically will be a battery. In order to increase the life of electronic unit 14, power supply 70 may be a lithium battery of the type used in cardiac pacemakers. In order to further reduce the power drain on power supply 70, each of the electronic modules shown in FIG. 3 may be constructed of CMOS fabrication technology. As is well known, CMOS circuits draw very little current while in the nonswitching state. To further reduce the power drain on power supply 70, a pulse signal from time clock 58 may be provided in conjunction with the internal reset pulse initiating action by microprocessor 52 in order to enable certain of the modules, such as analog to digital converter 62, multiplexers and amplifiers 60, and program storage 54. Thus, these components will only receive power from power supply 70 during the time their actual operation is required. Certain other components must always receive power, such as microprocessor 52 and data storage 56 so that the data memory can continually be refreshed.

Figure 4:
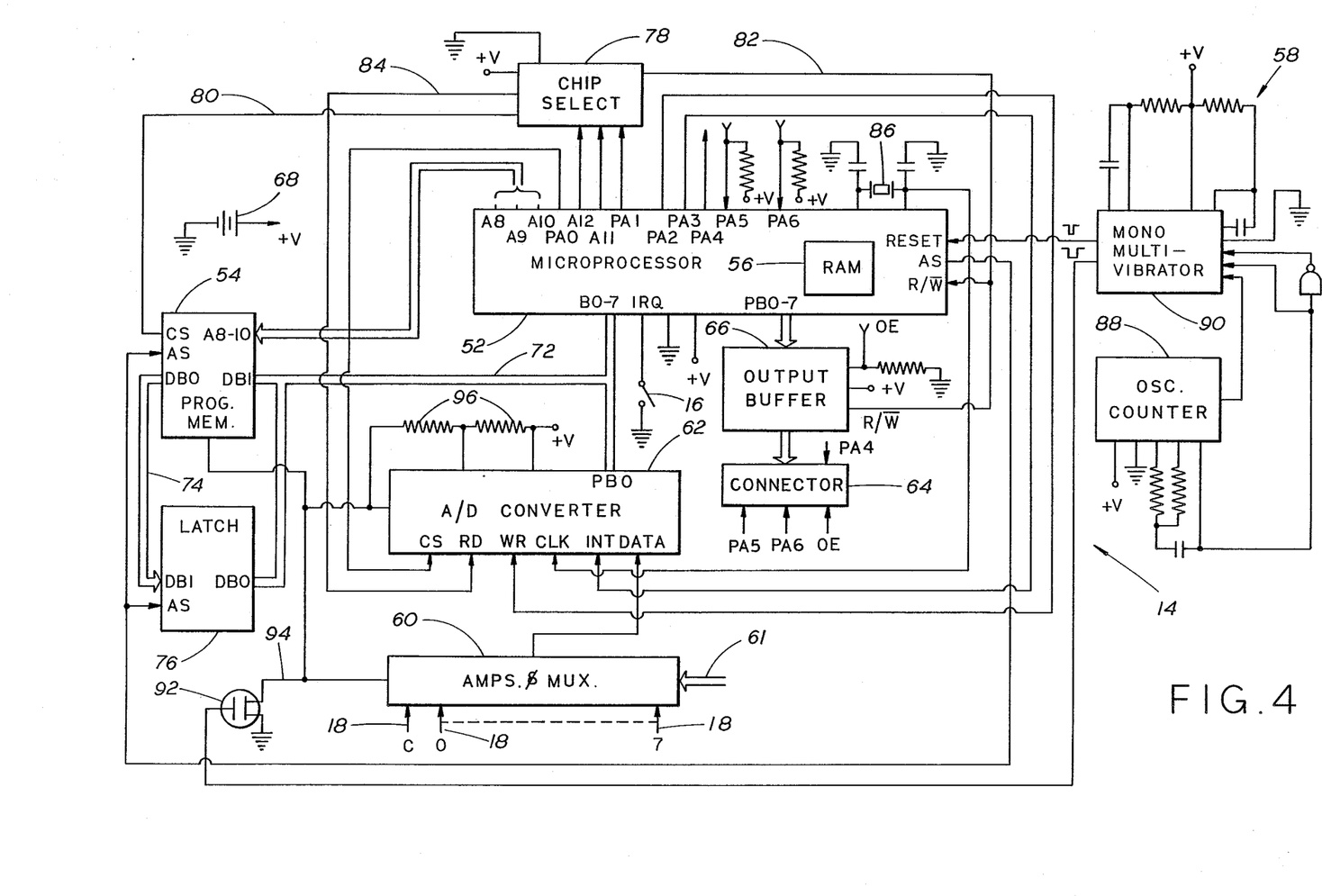
FIG. 4 shows a circuit diagram of the electronic unit of the subject invention.

Referring now to FIG. 4, a more detailed diagram of electronic unit 14 is shown. Microprocessor 52 is shown as including internal therewith the random access memory data storage memory 56. Microprocessor 52 may be an MC146805 microprocessor module. It is well known that such a module includes an output port containing eight lines labeled PB0 through PB7. In addition, microprocessor 52 contains an eight line data bus input, B0 through B7, a five line, address bus, A8 through A12, and an address output port PA0-PA7. Other control lines included with microprocessor 52 include an interrupt request input (IRQ), a reset input (RESET), an address strobe output (AS), and a read or write input labeled R/W.

Switch 16 is coupled between ground and the IRQ input of microprocessor 52. Upon depression of switch 16, the IRQ input is grounded, causing an interrupt of microprocessor 52 to occur. This interrupt resets microprocessor 52 to read the first addressed instruction from program memory 54, which, in turn, enables the reset input to respond to the sample signals from clock 58. The instruction is provided to microprocessor 52 over data bus 72.

Program memory 54 includes data bus input (DBI) which consists of eight input lines connected to receive the data on data bus 72. In addition, program memory 54 includes a data bus output line (DBO) consisting of eight individual lines to which is provided the data stored in program memory 54. Further, program memory 54 includes a chip select (CS) input and an address strobe (AS) input, as well as three address line inputs A8 through A10. The A8 through A10 outputs from microprocessor 52 are coupled to the A8 through A10 inputs of program memory 54. This information, plus the information contained on data bus 72 during the provision of the AS signal addresses one byte of information contained in program memory 54. The addressed information is then provided over the output data bus 74 from program memory means 54 upon application to program memory 54.

The signal provided from program memory 54 to output data bus 74 is provided to latch circuits 76. Latch circuits 76 includes eight latches, one for each of the lines of bus 74. In addition, latch circuits 76 respond to the address strobe (AS) signal by latching the address on bus 74 for subsequent provision therein and providing at its DBO output. Microprocessor 52 can then read the data provided from the output of latches 76 to data bus 72 to receive the next instruction.

Chip select circuit 78 functions to chip select various circuits in FIG. 4 upon command of microprocessor 52. Circuit 78 may be a conventional decoder circuit or a read only memory and is controlled by the A11, A12 and PA1 lines from microprocessor 52 which address an appropriate signal therefrom. One of the outputs from chip select circuit 78 is provided over line 80 to the chip select (CS) input of program memory 54 and can be used to control the response of program memory 54 to incoming addressing data thereto. Another output line 82 from chip select circuit 78 is provided to the read/write (R/W) inputs of both microprocessor 52 and output buffer 66 to control when data is transmitted from circuit 14 through connector 64 to an attached output device.

Analog to digital converter 62 has a chip select (CS), read (RD), write (WR), clock (CLK), interupt (INT), and data (DATA) inputs thereto. The CS input of A/D converter 62 is coupled to the PA0 line from microprocessor 52; the RD input of A/D converter 62 is coupled to line 84 from chip select circuit 78; the WR input of A/D converter 62 is coupled to the PA2 output from microprocessor 52; the CLK input to A/D converter 62 is coupled from one end of crystal 86 used to control the clock signals provided to microprocessor 52; the INT input to A/D converter 62 is provided from the PA3 output of microprocessor 52. The DATA input of A/D converter 62 receives analog data from the amplifiers and multiplexers 60. In addition, appropriate voltage and ground signals are provided to A/D converter 62. The operation of A/D converter 62 is controlled in a known manner by the various signals provided thereto over the CS, RD, WR, CLK and INT inputs to receive the analog data from block 60 and convert it to an eight-bit digital signal for provision from its output (DBO) to data bus 72.

Amplifiers and multiplexers 60 receive each of the temperature sensing lead 18 signals from electrode unit 12. These signals include both the common signal from the common electrode and eight signals from each of the testing electrodes. The eight signals from the testing electrodes are labeled 0 through 7 and the signal from the common electrode is labeled as C. These signals are amplified by amplifiers included within circuit 60 and provided to differential amplifiers to determine the analog difference between the testing electrode signals, and the common electrode signal. The multiplexer portion of circuit 60 selects one of the eight outputs from the differential amplifiers and provides it to the DATA input of A/D converter 62. The selection is under the control of microprocessor to control the selection of the particular multiplexer line. Through instructions to microprocessor 52, a number from 0 to 8 is written into multiplexer 60 from the microprocessor 52 over line 61. The number is latched and closes 1 of 9 switches in multiplexer 60 thereby connecting 1 of 9 thermistors to a common amplifier. The amplifier output is connected to the A/D input which converts the temperature into a digital value.

Real time clock 58 includes and oscillator counter 88 and a dual stage monostable multivibrator 90. Oscillator counter 88 includes appropriate resistors and capacitors to cause it to oscillate at a frequency of 540 Hz. Internal to oscillator counter 88 is a counter which causes a pulse to be provided periodically therefrom such as every thirty seconds. The pulses from oscillator counter 88 are provided to each of the dual monostable multivibrators in circuit 90. The first pulse is a short duration pulse provided to the RESET input of microprocessor 52. The second pulse from monostable multivibrator 90 is a longer duration pulse having a leading edge coincident with the leading edge of the shorter duration pulse. This longer duration pulse from circuit 90 is used to enable the power to be applied to various of the chips in circuit 14 only during the time necessary for their operation. Monostable multivibrator circuit 90 also includes appropriate resistors and capacitors and power supply connections to control the duration of the pulses provided thereby.

Output buffer 66 receives output data from the PBO through PB7 outputs of microprocessor 52. Upon appropriate application of R/W signal from chip select circuit 78 output buffer 66 provides these signals to connector 64. In addition, the PA4, PA5, PA6 and output enables (OE) signals are provided to connector 64 to control the attached output means, which may be a printer, plotter or keyboard display terminal unit, useful to display the information stored in RAM 56. By providing the appropriate control signals from microprocessor 52 to connector 66 microprocessor 52 can control the operation of the output device. In addition the output device may have its own internal processing power to further control the information, but the master control remains with microprocessor 52.

Battery 68, which may be a long-life lithium battery, provides both a +V and ground signals to each of the various modules shown in circuit 14. In order to increase the life of battery 68, certain of the modules can remain off, except during the time they are actually receiving or processing information. For example, where circuit 14 is used to control the allergy testing of a patient, it may only operate for a few miliseconds every thirty seconds. During the period in which circuit 14 is not operating, it is desirable to turn off power to program memory 54, A/D converter 62, and amplifiers and multiplexer 60. Because the remaining components are constructed of CMOS technology, they draw very little power unless actually instructed to perform an operation and it may be unnecessary to eliminate the power thereto. In other instances, such as in the case of RAM 56, it is necessary to continually refresh the memory and power must continually be provided. The same is true of the oscillator circuit 86.

The longer duration pulse from monostable multivibrator 90 is provided to the gate electrode of an FET transistor 92. Upon application of a high voltage to the gate of transistor 92, the source drain path is rendered conductive causing a ground voltage to be provided over line 94. This causes a ground signal to be provided to program memory 54, A/D converter 62, and amplifiers and multiplexers 60, thereby disabling those devices. When transistor 92 is not conductive due to a low voltage from monostable multivibrator 90, the voltage from resistors 96 appears on line 94, enabling the devices. Thus, if the longer duration pulse from monostable multivibrator is a negative going signal, the normal power consuming device 54, 60 and 62 are only operational when needed.

Figures 5, 6:
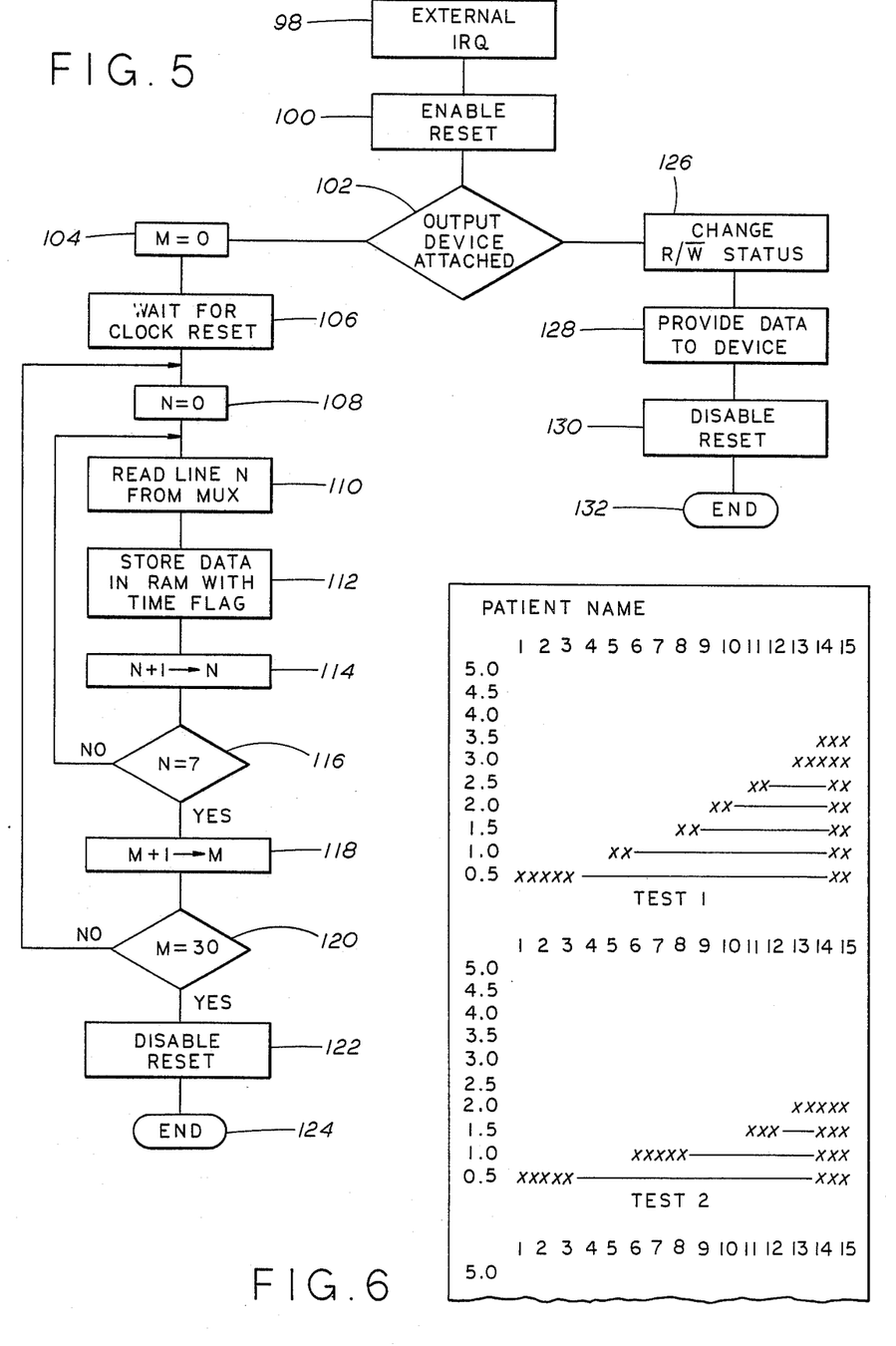
FIG. 5 shows a flow diagram of the instruction program used to control the microprocessor shown in FIG. 4.
FIG. 6 shows an example of a test print out which can be obtained by using the subject invention.

Referring now to FIG. 5, a flow diagram of the operation of electronic unit circuit 14 is shown. First, according to block 98, an external interrupt request occurs. This occurs as a result of the closure of switch 16 grounding the IRQ input of microprocessor 52. This initiates further action by microprocessor 52. Next, according to block 100, the RESET input is enabled to respond to signals provided thereto from monostable multivibrator 90. Only upon the occurence of each of the signals applied to the RESET input, further processing occurs as indicated below.

Next, according to block 102, a determination is made whether an output device is attached. This may be accomplished by polling a potential output device through connector 64 utilizing the PA5 or PA6 signals. If it is determined that no output device is attached, then according to block 104 the variable M is set equal to zero and according to block 106, a wait for the next clock reset signal from real time clock 58 occurs. Upon provision of the next signal to the RESET input of microprocessor 52 from monostable multivibrator 90, block 108 indicates the variable N is set equal to zero.

Then, according to block 110, line N from the multiplexer portion of circuit 60 is read. This occurs by microprocessor 52 setting multiplexer 60 to read line N. It should be noted that line N is one of the lines zero through seven applied from the testing electrodes over lines 18. Next, according to block 112, the data selected from multiplexer 16 is provided through A/D converter 62 and stored in RAM 56. In addition, a time flag is stored in conjunction with the data read. The time flag may be the variable M indicating which of the thirty readings is being stored. Next, according to block 114 the variable N is increased by one and according to block 116 a determination is made whether N is equal to seven. If not, the next line is selected in the multiplexer in circuit 30 and the process from blocks 110 through 116 is repeated.

When at block 116 it is determined that N is equal to seven, the final data line will have been read and a continuation of block 118 occurs. At this point the variable M is incremented by one and according to block 120, a determination is made whether M is equal to thirty to indicate the testing procedure is over. If not, a return to block 106 occurs and the next monostable multivibrator 90 reset signal is omitted. Upon its occurrence the steps from blocks 108 through 120 result. It should be noted that the number 30 can be made variable by appropriate operator controlled input devices, such as an attachable keyboard.

If at block 120 it were determined that M equalled thirty, thereby indicating that the testing sequence was over, a continuation at block 122 occurs and the RESET input of microprocessor 52 is disabled. Thereafter, the flow of the program ends as indicated by block 124.

Referring back to block 102, if it had been determined that an output device had been attached to connector 64, then according to block 126 the R/W status line is changed to allow the data to be transmitted thereby and according to block 128, the data is provided by microprocessor 52 from RAM 56 through output buffer 66 and output connector 64 to the output device. Thereafter, the RESET is disabled, as indicated by block 130, and the flow ends as indicated by 132.

Referring now to FIG. 6, an example of the type of printout which is useful to the physician to assist him in diagnosing an allergy condition is shown. This type of printout can be controlled either directly by microprocessor 52 or under the control of microprocessor 52 by special processors included in the output device. As seen from FIG. 6, each of the eight tests is individually printed. The X axis of the printout may include a time line from one to fifteen minutes. The Y axis may include the increase in temperature over the allergy reaction area as determined by the sensors 32 of the electrodes 26. In the case of test 1, performed by the first electrode, it is noted that a 0.5 degree rise in temperature occurred at the one minute time. Thereafter at three and one-half minutes, a one degree differential rise in temperature occurred and so forth, until at thirteen and one-half minutes a four degree increase in temperature was detected. For the test performed by the second electrode it is noted that at the twelve minute time only a two degree temperature rise was detected. The remaining tests 3 through 8 would include similar formatted print outs. The physician viewing the print out shown in FIG. 6 can, at a glance, easily determine the allergic reaction or non-allergic reaction manifested by the printout. Further, the physician can determine the degree of reaction by noting the slope of the graph.

In using the electrode 12 shown in FIGS. 1 and 2, the physician can test for eight different allergies or he can place different concentrations of allergen in each of the pads 42 of two or more electrodes. Then by viewing the slope of the print out as the temperature increases with time, the physician can determine more precisely the degree of the allergic reaction undergone by the patient 22. By using the electronic unit 14, the entire test is automatic, short term and without any pain to the patient. Further, since the amount of allergen actually injected into the body of patient 22 is substantially less than other tests, the chances of undesirable major reactions by the patient is substantially decreased.

What is claimed is:

1. A system for measuring allergic response, including:
   allergen delivery means for transcutaneously delivering an ionizable selected substance into the skin of a subject to test for allergic response of the subject to said substance, said means including charging and return electrodes positioned for spaced topical placement on the subject's skin effective to provide a conductive path through the tissue of the skin for transcutaneous transport of said selected substance, said charging electrode including a charging member responsive to a first electric signal and, in contact with said charging member, a medium for containing said selected substance, said medium being positioned to separate said charging member from contact with the skin upon said topical placement of said charging electrode;
   temperature sensing and signaling means adapted for placement in thermal contact with an area of skin of the subject at a location in juxtaposition with said path, for sensing instantaneous temperature of the skin at said location and for outputting a second electric signal manifesting said instantaneous temperature;
   processing control means for controlling the application of said first electric signal and for receiving and processing said second electric signal, said processing control means including sampling and storing means for sampling said second signal during a plurality of times and for storing data manifesting the sensed temperature for each sampling time, and
   means for providing an output of the stored data indicating change in temperature of said area of skin with respect to time.

2. The invention of claim 1 in which said temperature sensing and signaling means includes (a) thermal pickup means for sensing the temperature of the said area of skin, and (b) transducer means in thermal communication with said pickup means for converting said communicated sensed temperature into said second electric signal.

3. The invention of claim 2 in which said second electric signal is an analog signal having an instantaneous amplitude related to a sensed instantaneous temperature, wherein said processing control means includes analog to digital converter means for converting said received second electric signal into a digital signal, and wherein said sampling means includes clock means for generating a plurality of sampling signals each at a periodic interval to cause said sampling to automatically occur.

4. The invention of claim 3 in which said transducer means is a thermistor.

5. The invention according to claim 3 wherein said sampling and storing means includes microprocessor means and memory means, said microprocessor means responding to said sampling signals for reading digital data from said converter means and storing said read digital data in said memory means.

6. The invention according to claim 5 wherein said sampling and storing means further includes means to disable power application to said converter means and said process control means, except during said sampling time.

7. The invention according to claim 6, including means for application of said sampling signal to said microprocessor means and means responsive thereto to initiate a sampling and storing of said data by said microprocessor means only during the duration of said sampling signal, said microprocessor means being placed in an inactive state until the occurence of a next succeeding sampling signal.

8. The invention according to claim 7 wherein said means for providing an output includes connector means of a type adapted for connection to an output indicator means, said microprocessor means having means providing a signal to said connector means for controlling said output indicator means to indicate said output.

9. A system for measuring allergic response of the skin of a subject, comprising:
   containing means for containing a hydrolyzable allergen, said containing means having (i) a first surface adapted to contact said skin of a subject, and (ii) a second surface adapted to be contacted by a charging member;
   a charging member contacting said second surface of said allergen containing means;
   means for providing an electric charge to said allergen whereby said allergen is transcutaneously delivered to said subject;
   means adapted for placement in thermal contact with said skin at a test area proximate said allergen containing means, including (a) thermal pickup means for sensing instantaneous temperature of the said skin at said area, and (b) transducer means, in thermal communication with said pickup means, for converting said instantaneous temperature into an output signal manifesting said instantaneous temperature, said thermal pickup means having an opening therein within which, thermally and electrically insulated from said pickup means, said allergen containing means and said charging member are positioned;
   clock means for providing a plurality of sampling signals each at a predetermined periodic interval related to a desired frequency of sampling during a selected duration of measurement of temperature rate of change of an allergic response to be measured;
   storing means responsive to said output signal and each of said sampling signals for storing data indicating the temperature manifested by said output signal each time a sampling signal is provided; and
   output means coupled to said storing means for providing a readable relationship of the change in temperature of said test area during the said duration of measurement when said sampling signals were provided.

10. The invention according to claim 9 wherein said system further includes a return electrode positioned to contact the skin of the subject, said return electrode being positioned within said opening between said thermal pickup means and said allergen containing means and said charging member, thermally and electrically insulated from said pickup means and electrically insulated from said charging member and said allergen containing means.

11. The invention according to claim 9 wherein said clock means includes an oscillator, a counter and a monostable multivibrator for providing said sampling signal as an enable signal to enable said storing means only during a sampling interval substantially less than a predetermined time between a sampling signal and a next succeding sampling signal.

12. The invention according to claim 11 wherein said means for storing includes microprocessor means and data memory means, said data being obtained under control of said microprocessor means and stored in said memory means.

13. The invention according to claim 12:
   wherein said output signal is an analog signal having an amplitude manifesting said temperature; and
   wherein said means for storing includes an analog to digital converter means responsive to said output signal and control signals from said microrocessor means for converting said output signal into a digital signal manifesting said temperature only during provision of said sampling signals.

14. The invention according to claim 13 including means for application of said digital signal to said microprocessor means and microprocessor means responsive thereto for sending, only during provision of said sampling signal, a digital signal manifesting said temperature to be stored in said memory means.

15. The invention according to claim 12 wherein said output means includes indicator means responsive to control signals from said microprocessor means for receiving said data stored in said data memory means and for providing a visual manifestation of change of temperature of said test area with respect to time.

16. A system for measuring allergic response of the skin of a subject, comprising:
   a plurality of containing means for containing at least one hydrolyzable allergen in a plurality of spaced apart repository means, each said containing means having (i) a first surface adapted to contact a plurality of spaced apart areas of said skin of a subject and (ii) a second surface adapted to be contacted by a charging member;
   a charging member contacting said second surface of each said allergen containing means;
   means for providing an elecric charge to each said allergen whereby said allergen is transcutaneously delivered to said subject at each said area of skin;
   means adapted for placement in thermal contact with said skin at each said area of skin proximate each said allergen repository means, including (a) thermal pickup means for sensing instantaneous temperature of the said skin at each said area, and (b) transducer means, in thermal communication with each said pickup means, for converting said instantaneous temperature of each said area into an output signal manifesting each said instantaneous temperature of each said area, each said thermal pickup means having an opening therein within which, thermally and electrically insulated therefrom, said allergen repository means is positioned;
   clock means for providing a plurality of sampling signals each at a predetermined periodic interval related to a selected duration of measurement of temperature rate of change of an allergic response to be measured;
   storing means responsive to each said area output signal and each of said sampling signals for storing data indicating the temperature manifested by each said area output signal each time a sampling signal is provided; and
   output means coupled to said storing means for providing a readable relationship of the change in temperature of each said test area during the time said sampling signals are provided.

17. The invention according to claim 16 wherein said output means provides a readable relationship of the temperature of each of said test areas during each time said sampling signals are provided.

18. The invention according to claim 16 wherein said clock means includes an oscillator, a counter and a monostable multivibrator for providing said sampling signal as an enable signal to enable said storing means only during a sampling interval substantially less than a predetermined time between a sampling signal and a next succeeding sampling signal.

19. The invention according to claim 16 wherein said storing means includes microprocessor means and data memory means, said data being obtained responsive to control signals from said microprocessor means and stored in said memory means.

20. The invention according to claim 19:
wherein said output signal is an analog signal for each test area having an amplitude manifesting said temperature; and
wherein said storing means includes a multiplexer to which each of said output signals are provided, said multiplexer being controlled by said microprocessor means to provide a selected one of said output signals for storage in said data memory.

21. The invention according to claim 20 wherein said storing means further includes an analog to digital converter means responsive to said selected output signal and control signals from said microprocessor means for providing a digital signal of said selected output signal only during the provision of sampling signals.

22. The invention according to claim 21 including means for application of said digital signal to said microprocessor means and microprocessor means responsive thereto for sending, only during provision of said sampling signal, a digital signal manifesting said temperature to be stored in said memory means.

23. The invention according to claim 22 wherein said clock means includes an oscillator, a counter and a monostable multivibrator for providing said sampling signal as an enable signal to enable said storing means only during a sampling interval substantially less than a predetermined time between a sampling signal and a next succeding sampling signal.

24. The invention according to claim 21 wherein said output means includes indicator means responsive to control signals from said microprocessor means for receiving said data stored in said data memory means and for providing a visual manifestation of any change of temperature of each of said test areas with respect to time.

25. The invention according to claim 24 wherein said microprocessor means includes means for reading said converter means digital signal and storing data in said memory means related to said digital signal only during provision of said sampling signals.

26. The invention according to claim 25 wherein said clock means includes an oscillator, a counter and a monostable multivibrator for providing said sampling signal as an enable signal to enable said storing means only during a sampling interval substantially less than a predetermined time between a sampling signal and a next succeeding sampling signal.

27. A method of measuring allergic response of the skin of a subject, comprising
establishing a conductive path in skin tissue of the subject between (a) a charging electrode which includes an ionizable substance to be tested for allergenicity and (b) a spaced apart electrode, thereby to transport such substance transcutaneously into skin tissue in said path;
measuring instantaneous temperature of the skin surface of said subject proximate said conductive path for a plurality of times during a predetermined period of measurement for any allergic response of the subject to the substance; and
manifesting change of skin temperature with respect to time as an indication of degree of allergic response.

28. The method according to claim 27 wherein said step of manifesting includes visually indicating a relationship of said change of skin temperature with respect to time during said period.

29. The method according to claim 27 wherein said step of measuring includes the steps of sensing the temperature of said skin surface, converting the sensed temperature into an electric signal, providing said electric signal to processor means and storing data related to said provided signal in memory means under the control of said processor means.

30. The method according to claim 29 wherein said step of manifesting includes visually indicating said change of skin temperature with respect to time relationship.

31. The method according to claim 29 wherein said step of providing said electric signal to processor means includes the step of converting said signal from an analog signal to a digital signal for storage in said memory means.

32. The method according to claim 31 wherein said step of manifesting includes visually indicating said change of skin temperature with respect to time relationship.

33. A method of measuring allergic response of the skin of a subject, comprising
establishing a conductive path in skin tissue of the subject in each of a plurality of test areas between (a) a plurality of charging electrodes each of which includes an ionizable substance to be tested for allergenicity and (b) at least one spaced apart electrode, thereby to transport each such substance transcutaneously into skin tissue in each said test area;
measuring instantaneous temperature of the skin surface of each said test area for a plurality of times during a predetermined period of measurement for allergic response of the subject to a substance in a said test area; and
manifesting change of skin temperature with respect to time of each said test area as an indication of degree of allergic response of such subject at each said test area to the substance at such test area.

34. The method according to claim 33 wherein said step of manifesting includes visually indicating a relationship of said change of skin temperature with respect to time for each test area.

35. The method according to claim 33 wherein said step of measuring includes sensing the temperature of each test area, converting each sensed temperature into an electric signal, providing each electric signal to processor means and storing data related to each provided signal in memory means under the control of said processor means.

36. The method according to claim 35 wherein said step of manifesting includes visually indicating a relationship of said change of skin temperature with respect to time for each test area.

37. The method according to claim 35 wherein said step of providing said electric signal to processor means includes selecting each of said provided signals, one at a time, and converting each selected signal from an analog signal to a digital signal, for storage in said memory means.

38. The method according to claim 37 wherein said step of manifesting includes visually indicating a relationship of skin temperature change with respect to time for each test area.

39. The method according to claim 33 wherein each said electrode includes a different substance to be delivered to each test area, whereby a plurality of different allergic reactions are tested.

40. The method according to claim 33 wherein each said electrode includes different amounts of the same substance to be delivered allergens to each to each test area, whereby the extensiveness of the allergic reaction is tested.

41. The method according to claim 33:
wherein said step of measuring includes referencing each temperature to the normal skin temperature of said patient; and
wherein said step of manifesting includes manifesting the differential rise in temperature with respect to time relationship.

* * * * *